(12) United States Patent
Kallummil et al.

(10) Patent No.: US 11,815,454 B2
(45) Date of Patent: Nov. 14, 2023

(54) METHOD AND SYSTEM FOR OPTIMIZING MONTE CARLO SIMULATIONS FOR DIFFUSE REFLECTANCE SPECTROSCOPY

(71) Applicant: SAMSUNG ELECTRONICS CO., LTD., Suwon-si (KR)

(72) Inventors: Sreejith Kallummil, Bangalore (IN); Sujit Jos, Bangalore (IN); Ibrahim A, Bangalore (IN); Ka Ram Choi, Suwon-si (KR); Sang Kyu Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 339 days.

(21) Appl. No.: 17/187,141

(22) Filed: Feb. 26, 2021

(65) Prior Publication Data

US 2021/0302310 A1 Sep. 30, 2021

(30) Foreign Application Priority Data

Mar. 27, 2020 (IN) .............................. 202041013480
Nov. 30, 2020 (KR) ........................ 10-2020-0164508

(51) Int. Cl.
*G01N 21/47* (2006.01)
*G06T 7/00* (2017.01)
(Continued)

(52) U.S. Cl.
CPC ..... *G01N 21/4738* (2013.01); *A61B 5/14532* (2013.01); *G06N 20/00* (2019.01); *G06T 7/0012* (2013.01)

(58) Field of Classification Search
CPC ............ G01N 21/4738; A61B 5/14532; A61B 5/002; A61B 5/7475; A61B 5/0022;
(Continued)

(56) References Cited

U.S. PATENT DOCUMENTS 6,285,690 B1 * 9/2001 Kim ...................... H01S 3/0903
372/2
8,804,115 B2 * 8/2014 Yu ............................ G01J 3/28
356/302

(Continued)

OTHER PUBLICATIONS

Ricky Hennessy et al., "Monte Carlo lookup table-based inverse model for extracting optical properties from tissue-simulating phantoms using diffuse reflectance spectroscopy", Journal of Biomedical Optics, vol. 18, 3, DOI: 10.1117/1.JBO.18.3.037003, Mar. 1, 2013, pp. 1-4, 5 pages total.

(Continued)

Primary Examiner — Md M Rahman
(74) Attorney, Agent, or Firm — Sughrue Mion, PLLC (57) ABSTRACT

A method of transforming Monte Carlo (MC) simulations for diffuse reflectance spectroscopy (DRS) may include obtaining, by a DRS device, MC simulated DRS measurements using a pre-defined number of photons; pre-processing, by the DRS device, the MC simulated DRS measurements to obtain normalized DRS measurements; correcting, by the DRS device, non-monotonicity of the normalized DRS measurements to obtain monotonic DRS measurements; converting, by the DRS device, the monotonic DRS measurements to a logarithmic domain to obtain logarithmic DRS measurements; performing, by the DRS device, curve fitting on the logarithmic DRS measurements in the logarithmic domain to obtain curve-fitted logarithmic DRS measurements; and transforming, by the DRS device, the curve-fitted logarithmic DRS measurements to a non-logarithmic domain to obtain transformed MC simulated DRS measurements.

14 Claims, 4 Drawing Sheets

(51) Int. Cl.
*G06N 20/00* (2019.01)
*A61B 5/145* (2006.01)

(58) Field of Classification Search
CPC .... A61B 5/0075; A61B 5/1455; G06N 20/00; G06N 7/01; G06T 7/0012
USPC ......................................................... 356/446
See application file for complete search history.

(56) References Cited

U.S. PATENT DOCUMENTS

| | | | |
|---|---|---|---|
| 9,554,738 B1* | 1/2017 | Gulati | A61B 5/0075 |
| 10,837,757 B1* | 11/2020 | Ikebuchi | G01B 11/007 |
| 2006/0211927 A1 | 9/2006 | Acosta et al. | |
| 2007/0282575 A1* | 12/2007 | Gossage | G06F 30/20 |
| | | | 703/2 |
| 2008/0270091 A1* | 10/2008 | Ramanujam | G01N 21/49 |
| | | | 703/6 |
| 2009/0073439 A1* | 3/2009 | Tearney | A61B 5/02007 |
| | | | 385/119 |
| 2010/0230602 A1 | 9/2010 | Scheins | |
| 2010/0305873 A1 | 12/2010 | Sjoden et al. | |
| 2011/0105865 A1* | 5/2011 | Yu | A61B 5/0059 |
| | | | 600/310 |
| 2014/0176678 A1 | 6/2014 | Novikau et al. | |
| 2015/0046090 A1* | 2/2015 | Chieffo | G01N 33/241 |
| | | | 702/2 |
| 2015/0186796 A1* | 7/2015 | Fischbacher | G16B 40/20 |
| | | | 706/12 |
| 2015/0364635 A1* | 12/2015 | Bodlovic | H01L 31/024 |
| | | | 250/214.1 |
| 2016/0097716 A1* | 4/2016 | Gulati | A61B 5/1495 |
| | | | 250/340 |
| 2016/0192896 A1 | 7/2016 | Perkins et al. | |
| 2018/0059259 A1 | 3/2018 | Carrel et al. | |
| 2019/0073802 A1 | 3/2019 | Case et al. | |
| 2019/0231193 A1* | 8/2019 | Hendon | A61B 5/0086 |
| 2020/0073909 A1* | 3/2020 | Kumar | G06T 7/55 |
| 2022/0001193 A1* | 1/2022 | Zhu | A61N 5/062 |

OTHER PUBLICATIONS

Ernesto Mainegra-Hing et al., "Fast Monte Carlo calculation of scatter corrections for CBCT images", Journal of Physics: Conference Series, 102, doi: 10.1088/1742-6596/102/1/012017, 2008, pp. 1-6, 7 pages total.

I El Naqa et al., "A comparison of Monte Carlo dose calculation denoising techniques", Phys. Med. Biol., 50, doi: 10.1088/0031-9155/50/5/014, Feb. 17, 2005, pp. 909-922, 15 pages total.

* cited by examiner

METHOD AND SYSTEM FOR OPTIMIZING MONTE CARLO SIMULATIONS FOR DIFFUSE REFLECTANCE SPECTROSCOPY

CROSS-REFERENCE TO RELATED APPLICATION(S)

This application is based on and claims priority under 35 U.S.C. § 119 to Indian Patent Application No. 202041013480 filed on Mar. 27, 2020, in the Indian Patent Office and to Patent Application No. 10-2020-0164508 filed in the Korean Patent Office on Nov. 30, 2020, the disclosures of which are incorporated by reference herein in their entireties.

TECHNICAL FIELD

The present disclosure is related in general to the field of spectroscopy and, more particularly but not exclusively to, a method and a system for optimizing Monte Carlo simulations for diffuse reflectance spectroscopy.

BACKGROUND

Diffuse Reflectance Spectroscopy (DRS) is a useful non-invasive technique to measure blood components such as glucose. There are two methods to estimate optical parameters (OP) containing glucose information from DRS measurements. The first method includes running Monte Carlo (MC) simulations with a photon count of substantially one hundred million (i.e., $=10^8$ photons) in an iterative loop. Thereafter, the MC simulations are matched with the DRS measurements to estimate optical properties. The second method includes running machine learning algorithms trained on 10,000-50,000 pairs of OP and DRS measurements generated using MC simulations. However, both of these methods are computationally demanding even with powerful graphics processing units, and are enormously time-consuming. For instance, the first method has zero offline complexity but has high runtime complexity. The second method has low runtime complexity but has high offline complexity since it has to generate 10,000-50,000 pairs of OP and DRS measurements.

The information disclosed in this background of the disclosure section is only for enhancement of understanding of the general background of the present disclosure and should not be taken as an acknowledgement or any form of suggestion that this information forms the prior art already known to a person skilled in the art.

SUMMARY

According to an aspect of an example embodiment, a method of transforming Monte Carlo (MC) simulations for diffuse reflectance spectroscopy (DRS) may include obtaining, by a DRS device, MC simulated DRS measurements using a pre-defined number of photons; pre-processing, by the DRS device, the MC simulated DRS measurements to obtain normalized DRS measurements; correcting, by the DRS device, non-monotonicity of the normalized DRS measurements to obtain monotonic DRS measurements; converting, by the DRS device, the monotonic DRS measurements to a logarithmic domain to obtain logarithmic DRS measurements; performing, by the DRS device, curve fitting on the logarithmic DRS measurements in the logarithmic domain to obtain curve-fitted logarithmic DRS measurements; and transforming, by the DRS device, the curve-fitted logarithmic DRS measurements to a non-logarithmic domain to obtain transformed MC simulated DRS measurements.

According to an aspect of an example embodiment, a diffuse reflectance spectroscopy (DRS) device for transforming Monte Carlo (MC) simulations for DRS may include a memory configured to store instructions; and a processor configured to execute the instructions to: obtain MC simulated DRS measurements using a pre-defined number of photons; pre-process the MC simulated DRS measurements to obtain normalized DRS measurements; correct non-monotonicity of the normalized DRS measurements to obtain monotonic DRS measurements; convert the monotonic DRS measurements to a logarithmic domain to obtain logarithmic DRS measurements; perform curve fitting on the logarithmic DRS measurements in the logarithmic domain to obtain curve-fitted logarithmic DRS measurements; and transform the curve-fitted logarithmic DRS measurements to a non-logarithmic domain to obtain transformed MC simulated DRS measurements.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The above and other aspects, features, and advantages of certain embodiments of the present disclosure will be more apparent from the following description taken in conjunction with the accompanying drawings, in which.

It should be appreciated by those skilled in the art that any block diagrams herein represent conceptual views of illustrative systems embodying the principles of the present disclosure. Similarly, it will be appreciated that any flowcharts, flow diagrams, state transition diagrams, pseudo code, and the like, represent various processes which may be substantially implemented by instructions stored on a non-transitory computer-readable medium and executed by a computer or processor.

DETAILED DESCRIPTION

In the present disclosure, the word "exemplary" is used herein to mean "serving as an example, instance, or illustration." Any embodiment or implementation of the present disclosure described herein as "exemplary" is not necessarily to be construed as preferred or advantageous over other embodiments.

While the disclosure is susceptible to various modifications and alternative forms, specific embodiments thereof have been shown by way of example in the drawings and will be described in detail below. It should be understood, however, that it is not intended to limit the disclosure to the particular forms disclosed, but on the contrary, the disclosure is to cover all modifications, equivalents, and alternatives falling within the scope of the disclosure.

The terms "comprises," "comprising," or any other variations thereof, are intended to cover a non-exclusive inclusion, such that a setup, device, or method that comprises a list of components or steps might not include only those components or steps but may include other components or steps not expressly listed or inherent to such setup, device, or method. In other words, one or more elements in a system or apparatus proceeded by "comprises" does not, without more constraints, preclude the existence of other elements or additional elements in the system or apparatus.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Embodiments of the present disclosure relate to a method and a system for optimizing Monte Carlo (MC) simulations for diffuse reflectance spectroscopy (DRS). Typically, for extracting parameters from DRS experimental measurements, MC simulated DRS measurements are used. The MC simulations are carried out using hundreds of millions of photons (e.g., $10^8$ photons) to obtain simulated measurements, which are similar to the experimental measurements. The MC simulation using hundreds of millions of photons requires a great deal of processing power and, hence, it is very time-consuming. The present disclosure optimizes the MC simulated measurements by using tens of thousands of photons instead of hundreds of millions of photons. Since the MC simulated measurements using tens of thousands of photons is noisy, the present disclosure implements multiple processing steps, which are low in complexity and require less processing time, thereby, providing an optimized method for Monte Carlo simulations for the DRS.

Figure 1:
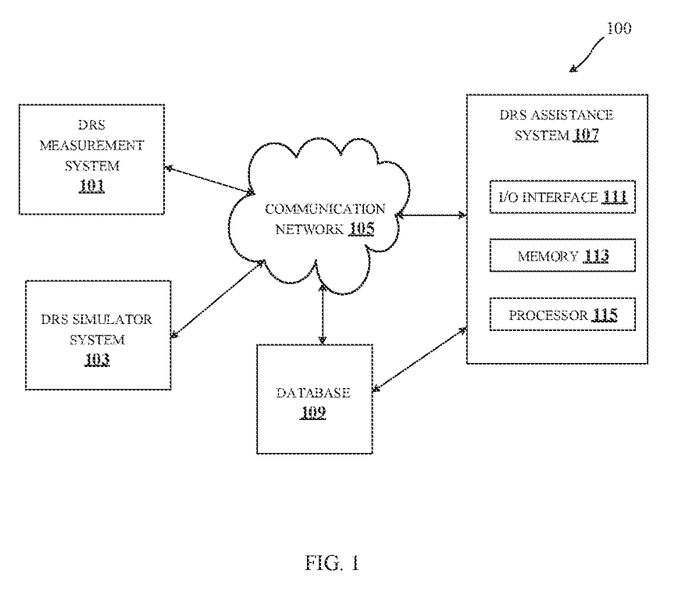
FIG. 1 illustrates an exemplary environment for optimizing MC simulations for DRS according to an example embodiment.

FIG. 1 illustrates an exemplary environment for optimizing MC simulations for DRS according to an example embodiment.

As shown in the FIG. 1, the environment 100 includes a DRS measurement system 101, a DRS simulator system 103, a communication network 105, a DRS assistance system 107, and a database 109. The DRS measurement system 101 and the DRS simulator system 103 may be connected through the communication network 105 to the DRS assistance system 107. In an embodiment, the DRS measurement system 101 may provide experimental DRS measurements taken on a sample. Here, the sample may be a portion of skin on which the DRS measurements are carried out in a non-invasive manner. The sample may be measured for gathering reflectance spectra from which essential skin optical properties revealing blood components, especially glucose, are acquired. Here, the DRS measurement system 101 may provide the DRS measurements in real-time to the DRS assistance system 107 via the communication network 105. In an embodiment, the DRS simulator system 103 may provide Monte Carlo (MC) simulated DRS measurements using a pre-defined number of photons in real-time to the DRS assistance system 107 via the communication network 105. As an example, here, the pre-defined number of photons considered is substantially ten thousand (e.g., $10^4$ photons). In an embodiment, during training, the DRS simulator system 103 may provide MC simulated DRS measurements using hundreds of millions of photons. Using the MC simulated DRS measurements, pre-defined parameters (described elsewhere herein) may be extracted. Here, the training may be carried out in an offline manner. The communication network 105 may include, but is not limited to, a direct interconnection, a Peer-to-Peer (P2P) network, a Local Area Network (LAN), a Wide Area Network (WAN), a wireless network (e.g., using Wireless Application Protocol), the Internet, a wireless fidelity (Wi-Fi) network, a Bluetooth network, and the like.

In an exemplary embodiment, the DRS assistance system 107 may obtain or receive the MC simulated DRS measurements using the pre-defined number of photons from the DRS simulator system 103. Subsequently, the DRS assistance system 107 may process the MC simulated DRS measurements in several steps to obtain tuned MC simulated DRS measurements. Lastly, the DRS assistance system 107 may extract optical parameters by comparing the tuned MC simulated DRS measurements and the experimental DRS measurements received from the DRS measurement system 101. The DRS assistance system 107 may include an Input/Output (I/O) interface 111, a memory 113, and a processor 115. The I/O interface 111 may be configured to receive the MC simulated DRS measurements from the DRS simulator system 103 and the experimental DRS measurements from the DRS measurement system 101. The I/O interface 111 may be configured to extract optical parameters by comparing the tuned MC simulated DRS measurements and the experimental DRS measurements and present the extract optical parameters. The I/O interface 111 may employ communication protocols/methods such as, without limitation, audio, analog, digital, monoaural, Radio Corporation of America (RCA) connector, stereo, IEEE-1394 high speed serial bus, serial bus, Universal Serial Bus (USB), infrared, Personal System/2 (PS/2) port, Bayonet Neill-Concelman (BNC) connector, coaxial, component, composite, Digital Visual Interface (DVI), High-Definition Multimedia Interface (HDMI), Radio Frequency (RF) antennas, S-Video, Video Graphics Array (VGA), IEEE 802.11b/g/n/x, Bluetooth, cellular (e.g., Code-Division Multiple Access (CDMA), High-Speed Packet Access (HSPA+), Global System for Mobile communications (GSM), Long-Term Evolution (LTE), Worldwide interoperability for Microwave access (WiMax), or the like.

The MC simulated DRS measurements from the DRS simulator system 103 and the experimental DRS measurements from the DRS measurement system 101 received by the I/O interface 111 may be stored in the memory 113. The memory 113 may be communicatively coupled to the processor 115 of the DRS assistance system 107. The memory 113 may, also, store processor instructions which may cause the processor 115 to execute the instructions for optimizing MC simulations for the DRS. The memory 113 may include, without limitation, memory drives, removable disc drives, etc. The memory drives may further include a drum, magnetic disc drive, magneto-optical drive, optical drive, Redundant Array of Independent Discs (RAID), solid-state memory devices, solid-state drives, etc.

The processor 115 may include at least one data processor for optimizing MC simulations for the DRS. The processor 115 may include specialized processing units such as integrated system (bus) controllers, memory management control units, floating point units, graphics processing units, digital signal processing units, etc.

In an exemplary embodiment, the DRS assistance system 107 may exchange data with the database 109 directly or through the communication network 105. The database 109 may be populated or stored with data that includes at least one of pre-defined parameters, the MC simulated DRS measurements, the experimental DRS measurements and optical parameters extracted by comparing tuned MC simulated DRS measurements and the experimental DRS measurements. Here, the pre-defined parameters are obtained from MC simulated DRS measurements using hundreds of millions of photons during training.

The database 109 may, also, be updated by the DRS assistance system 107 at a regular interval of time or at any time. These updates may be related to at least one of the MC simulated DRS measurements, the experimental DRS measurements and the optical parameters extracted by comparing the tuned MC simulated DRS measurements and the experimental DRS measurements.

Figure 2:
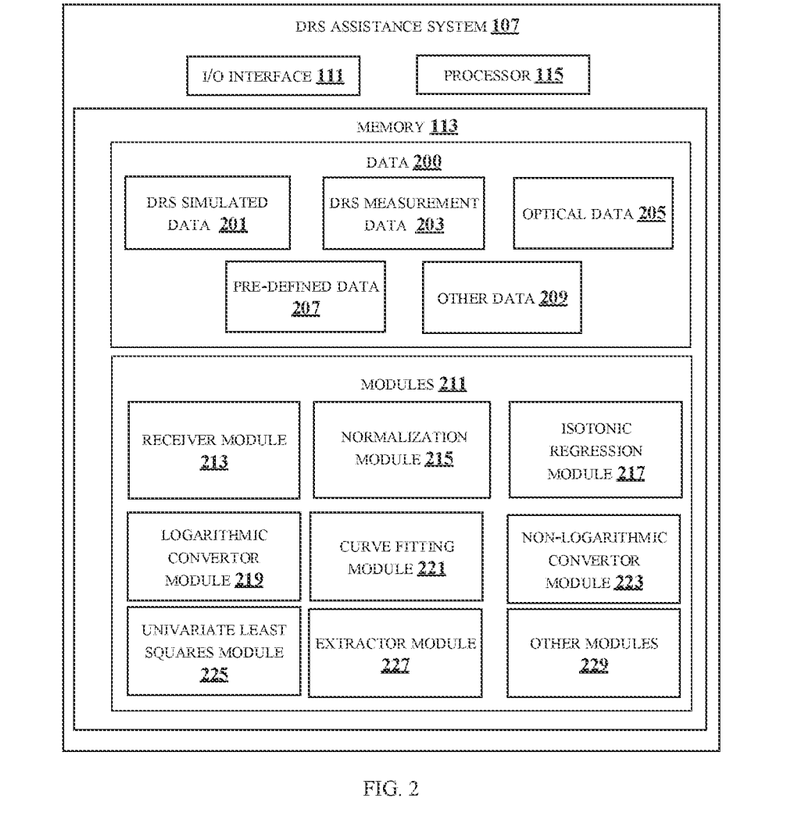
FIG. 2 shows a detailed block diagram of a DRS assistance system according to an example embodiment.

FIG. 2 shows a detailed block diagram of a DRS assistance system in accordance with some embodiments of the present disclosure.

The DRS assistance system 107, in addition to the I/O interface 111 and the processor 115 described above, may include data 200 and one or more modules 211, which are described herein in detail. In an embodiment, the data 200 may be stored within the memory 113. The data 200 may include, for example, DRS simulated data 201, DRS measurement data 203, optical data 205, pre-defined data 207 and other data 209.

The DRS simulated data 201 may include MC simulated DRS measurements using a pre-defined number of photons. Here, the pre-defined number of photons used for MC simulation is substantially ten thousand (e.g., $10^4$ photons).

The DRS measurement data 203 may include experimental DRS measurements. Here, the optimum number of photons used for experimental DRS measurements is substantially one hundred million photons (e.g., $10^8$ photons).

The optical data 205 may include optical parameters extracted by comparing tuned MC simulated DRS measurements obtained by processing the MC simulated DRS measurements in several steps and the experimental DRS measurements.

The pre-defined data 207 may include pre-defined parameters. Here, the pre-defined parameters are obtained from MC simulated DRS measurements using hundreds of millions of photons during training.

The other data 209 may store data, including temporary data and temporary files, generated by modules 211 for performing various functions of the DRS assistance system 107.

In an embodiment, the data 200 in the memory 113 are processed by the one or more modules 211 present within the memory 113 of the DRS assistance system 107. In the embodiment, the one or more modules 211 may be implemented as dedicated hardware units. As used herein, the term "module" refers to an Application Specific Integrated Circuit (ASIC), an electronic circuit, a Field-Programmable Gate Arrays (FPGA), Programmable System-on-Chip (PSoC), a combinational logic circuit, and/or other suitable components that provide the described functionality. In some implementations, the one or more modules 211 may be communicatively coupled to the processor 115 for performing one or more functions of the DRS assistance system 107. The said modules 211 when configured with the functionality defined in the present disclosure will result in a novel hardware.

In an implementation, the one or more modules 211 may include, but are not limited to, a receiver module 213, a normalization module 215, an isotonic regression module 217, a logarithmic converter module 219, a curve fitting module 221, an non-logarithmic converter module 223, an univariate least squares module 225 and an extractor module 227. The one or more modules 211 may, also, include other modules 229 to perform various miscellaneous functionalities of the DRS assistance system 107.

The receiver module 213 may receive the pre-defined parameters during training to be stored in the pre-defined data 207. In real-time, the receiver module 213 may receive or obtain MC simulated DRS measurements using a pre-defined number of photons. Here, the pre-defined number of photons is substantially ten thousand (e.g., $10^4$ photons).

The normalization module 215 may perform pre-processing on the MC simulated DRS measurements received from the receiver module 213 to obtain normalized DRS measurements. Here, the term "measurement" may, also, be referred to as "data." This is explained as follows: the MC simulated DRS measurements may be referred to as "DR4" as the pre-defined number of photons used for these measurements is substantially ten thousand (e.g., $10^4$ photons). The experimental DRS measurements may be referred to as "DR8" as the optimum number of photons used for these measurements is substantially one hundred million (e.g., $10^8$ photons). Since DRS technique involves several detectors, both DR4 and DR8 are N×1 vectors each. Here, N represents the number of detectors used to capture DRS results. Further, R is an N×1 vector specifying the distance of detectors from a radiation or a light source of the DRS. The measurement DR8[k] or DR4[k] is a reflectance captured by the kth detector at distance R[k]. The detectors are placed within the DRS setup such that R[1]<R[2]< . . . <R[N]. The normalization module 215 normalizes DR8 and DR4. The normalized DR8 and DR4 are represented as $DR8_{norm}$ and $DR4_{norm}$, respectively. The normalization step is performed as shown below:

$$DR8_{norm} = DR8/DR8[1]$$

$$DR4_{norm} = DR4/DR4[1]$$

Here, $DR8_{norm}$ satisfies $DR8_{norm}[1]=1$ and $0 \leq DR8_{norm}[k] \leq 1$.

Similarly, $DR4_{norm}$ satisfies $DR4_{norm}[1]=1$ and $0 \leq DR4_{norm}[k] \leq 1$.

The above steps are pre-processing stages to improve the correlation between DR4 and DR8. In terms of information regarding optical parameters (OP), both DR8 and $DR8_{norm}$ are similar. Hence, there is no loss in approximating $DR8_{norm}$ instead of DR8 itself.

Typically, $DR8_{norm}[k]$ assumes a parametric form, which is given as following:

$$DR8_{norm}[k] \cong \exp(c_1\sqrt{R[k]-R[1]} + c_2(R[k]-R[1]) + c_3(R[k]-R[1])^2)$$

The parameters $c_1$, $c_2$ and $c_3$ are estimated from $DR4_{norm}$, which provides an accurate and smooth approximation to $DR8_{norm}$.

Typically, $DR4_{norm}[k]$, which is similar to $DR8_{norm}[k]$ is given below:

$$DR4_{norm}[k] \cong \exp(c_1\sqrt{R[k]-R[1]} + c_2(R[k]-R[1]) + c_3(R[k]-R[1])^2)$$

The isotonic regression module 217 may perform the step of correcting non-monotonicity of the normalized DRS measurements using isotonic regression technique to obtain monotonic DRS measurements. Typically, it is empirically observed that the DRS including $DR8_{norm}$ decreases exponentially with the distance from a source of the DRS. As DR4 refers to tens of thousands of photons used for the MC simulated DRS measurements, which is much less than DR8 that uses hundreds of millions of photons, $DR4_{norm}$ is a low quality DRS and $DR4_{norm}[k]$ increases sometimes with increasing R[k]. Since $DR8_{norm}[k]$ is strictly decreasing, the $DR4_{norm}$ measurements needs to be non-increasing. This is achieved using an isotonic regression technique. Based on applying the isotonic regression technique, $DR4_{norm}$ measurements becomes monotonic DRS measurements. That is, the monotonic DRS measurements decrease with an increasing R[k]. Here, the monotonic DRS measurements may be represented as $DR4_{isotone}$. The isotonic regression operation performed is shown below:

$$DR4_{isotone} = \arg\min_{DR} \| DR - DR4_{norm} \|_2^2 \text{ s.t. } DR[1] \geq DR[2] \ldots \geq DR[N]$$

For example, if 2, 3, 1 represent non-monotonic DRS measurements, then after applying the isotonic regression technique, the outcome is 2, 1.5, 1, which are monotonic DRS measurements. The isotonic regression technique used here is extremely fast and involves very low complexity.

The $DR4_{isotone}$ measurements may have some measurement values as zero. This may be problematic when taking a logarithm of $DR4_{isotone}$ measurements. In view of this, the zero values in the $DR4_{isotone}$ measurements are replaced with the minimum non-zero value. For example, if 3, 2, 1, 0, 0 represent monotonic DRS measurements, then replacing the zero values with the minimum non-zero value gives 3, 2, 1, 1, 1. In this case, the monotonic DRS measurements may be called as $DR4_{nonzero}$.

The logarithmic converter module 219 may convert the monotonic DRS measurements $DR4_{nonzero}$ to the logarithmic domain to obtain logarithmic DRS measurements. $DR4_{norm}[k]$ is given below:

$$DR4_{norm}[k] \cong \exp(c_1 \sqrt{R[k]-R[1]} + c_2(R[k]-R[1]) + c_3(R[k]-R[1])^2)$$

Taking a logarithm of $DR4_{norm}[k]$ gives the following expression, which is an output of the logarithmic converter module 219:

$$y[k] = \log(DR4_{nonzero}[k]) \cong c_1 \sqrt{R[k]-R[1]} + c_2(R[k]-R[1]) + c_3(R[k]-R[1])^2$$

The curve fitting module 221 may perform curve fitting on the logarithmic DRS measurements in the logarithmic domain using a least squares technique and pre-defined parameters.

$$y[k] = \log(DR4_{nonzero}[k]) \cong c_1 \sqrt{R[k]-R[1]} + c_2(R[k]-R[1]) + c_3(R[k]-R[1])^2$$

From the above equation, the parameters $c_1$, $c_2$ and $c_3$ are estimated in the logarithmic domain as follows:

Initially, N×3 matrix and $X = [\sqrt{R-R[1]}, R-R[1], (R-R[1])^2]$ is defined. Then y[k] is represented in matrix form as $y \cong Xc$, which is a classical linear regression model.

The vector $c = [c_1 \ c_2 \ c_3]^T$ is estimated using a regularized least squares technique where $$c = \lambda_1 (X^T X + \lambda_1 I)^{-1} c_{prior} + (X^T X + \lambda_1 I)^{-1} X^T \frac{(y + \lambda_2 y_{prior})}{1 + \lambda_2}.$$

Here $y_{prior}$ and $c_{prior}$ are prior values used to improve the estimation of c and reduce noise in y. The $y_{prior}$ and $c_{prior}$ are referred as the pre-defined parameters. The pre-defined parameters are calculated offline from $DR8_{norm}$ during training.

The $y_{prior}$ is calculated as an average of 10 different values of $\log(DR8_{norm})$. To compute $y_{prior}$, the following steps are carried out:

The step 1 involves generating 10 pairs of (DR8, OP) using MC simulations with hundreds of millions of photons. In step 2, normalization of each pair of the 10 DR8 to get 10 $DR8_{norm}$ is carried out. In the final step, the logarithm of each of the 10 $DR8_{norm}$ (i.e., $\log(DR8_{norm})$) is obtained followed by taking an average of 10 different values of $\log(DR8_{norm})$, which gives the value of $y_{prior}$.

The $c_{prior}$ is calculated by taking least square estimates of c generated from $DR8_{norm}$. Computing $c_{prior}$ is as follows.

Initially, pairs of (DR8, OP) are generated using MC simulations with hundreds of millions of photons. For example, 10 pairs may be generated. Then, normalization of each pair of the 10 DR8 to get 10 $DR8_{norm}$ is carried out. A logarithm of each of the 10 $DR8_{norm}$ (i.e. $\log(DR8_{norm})$) is obtained. Then, for each of 10 $\log(DR8_{norm})$, the value of c is computed using following equation:

$$c = (X^T X + \lambda_1 I)^{-1} X^T \frac{(y + \lambda_2 y_{prior})}{1 + \lambda_2}$$

Finally, an average of 10 values of c are calculated to obtain $c_{prior}$. Here, typically, $y_{prior\_}$ is calculated first followed by $c_{prior}$.

The $y_{prior}$ and $c_{prior}$ parameters indicate what should have been the values of a typical c and y when using DR8 measurement instead of DR4 measurement.

The non-logarithmic converter module 223 may transform the logarithmic DRS measurements approximated using the least squares technique to the non-logarithmic domain to obtain optimized MC simulated DRS measurements. After the curve fitting step, $DR4_{smooth} = \exp(Xc)$ is performed, which is an estimate of $DR8_{norm}$. Here, $\exp(Xc)$ refers to exponential of (Xc). The $DR4_{smooth}$ is an optimized MC simulated DRS measurement.

The univariate least squares module 225 may apply a univariate least squares technique to the optimized MC simulated DRS measurements to obtain tuned MC simulated DRS measurements. The $DR4_{smooth}$ obtained from the non-logarithmic converter module 223 differs slightly from $DR8_{norm}$. In order to fine tune $DR4_{smooth}$, the univariate least squares technique is applied to produce a final estimate $DR4_{final}[k]$, which is given by $$DR4_{final}[k] = s_k DR4_{smooth}[k] + b_k \text{ for } k=1,2,\ldots N$$

Here, $s_k$ and $b_k$ are called scale factor and bias factor, respectively. These factors are estimated offline using univariate least squares using very few pairs of ($DR4_{smooth}$, $DR8_{norm}$). The $DR4_{final}[k]$, which is tuned MC simulated DRS measurements, is similar to $DR8_{norm}$. To compute $s_k$ and $b_k$, the following steps are performed:

Initially, 10 tuples of (DR8, DR4, OP) using MC simulations with hundreds of millions of photons and tens of thousands of photons, respectively, are generated. In a subsequent step, normalization of each of the 10 DR4 and DR8 outcomes is carried out to obtain 10 pairs of $DR8_{norm}$ and $DR4_{norm}$. This is followed by an isotonic regression technique and exponential curve fitting on each of the 10 $DR4_{norm}$ which are performed to obtain 10 values of $DR4_{smooth}$. In a concluding step, for each k, the values of $s_k$ and $b_k$ are obtained such that $s_k DR4_{smooth} + b_k \cong DR8_{norm}$. To achieve this, the values of $s_k$ and $b_k$ are found that minimizes the approximation error $$\sum_{i=1}^{10} (s_k DR4_{smooth_i}[k] + b_k - DR8_{norm\ i}[k])^2.$$

Here, $DR4_{smooth_i}$ is the $i^{th}$ $DR4_{smooth}$ sample and $DR8_{norm_i}$ is the $i^{th}$ $DR8_{norm}$. This optimization problem is solved in closed form giving values of $s_k$ and $b_k$ for each of the k=1, 2, . . . N detectors. Here, N represents the number of detectors used to capture DRS results. The values $s_k$ and $b_k$ are computed offline.

The extractor module 227 may extract optical parameters by comparing the tuned MC simulated DRS measurements and the experimental DRS measurements. In this step, the extractor module 227 may compare the $DR4_{final}[k]$ and $DR8_{norm}$.

Figure 3:
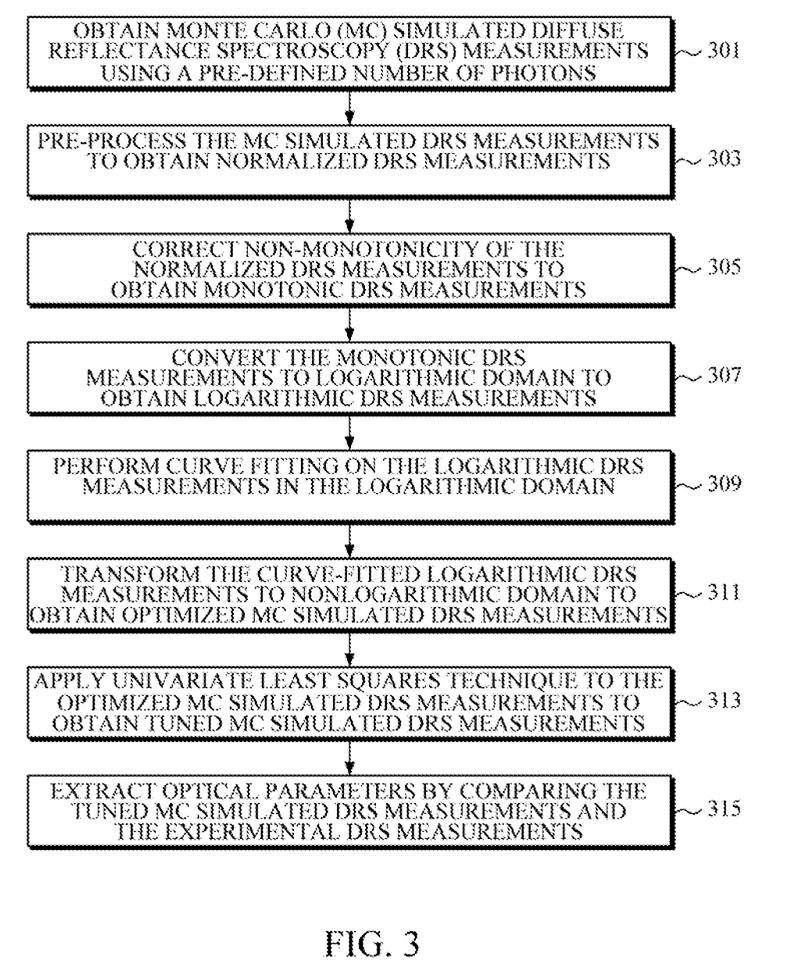
FIG. 3 illustrates a flowchart showing a method for optimizing MC simulations for DRS according to an example embodiment.

FIG. 3 illustrates a flowchart showing a method for optimizing MC simulations for DRS according to an embodiment.

As illustrated in FIG. 3, the method 300 includes one or more blocks for optimizing MC simulations for DRS. The method 300 may be described in the general context of computer executable instructions. Generally, computer executable instructions can include routines, programs, objects, components, data structures, procedures, modules, and functions, which perform particular functions or implement particular abstract data types.

The order in which the method 300 is described is not intended to be construed as a limitation, and any number of the described method blocks can be combined in any order to implement the method. Additionally, individual blocks may be deleted from the method 300 without departing from the scope of the subject matter described herein. Furthermore, the method 300 can be implemented in any suitable hardware, software, firmware, or combination thereof.

At block 301, the receiver module 213 may obtain MC simulated DRS measurements from the DRS simulator system 103 carried out using a pre-defined number of photons. Here, the pre-defined number of photons is less than an optimum number of photons used for experimental DRS measurements. As an example, the pre-defined number of photons is $10^4$ and the optimum number of photons used for experimental DRS measurements is substantially one hundred million (e.g., $10^8$ photons).

At block 303, the normalization module 215 may pre-process the MC simulated DRS measurements to obtain normalized DRS measurements.

At block 305, the isotonic regression module 217 may correct non-monotonicity of the normalized DRS measurements to obtain monotonic DRS measurements. The correcting of non-monotonicity of the normalized DRS measurement may be performed using an isotonic regression technique.

At block 307, the logarithmic convertor module 219 may convert the monotonic DRS measurements to the logarithmic domain to obtain logarithmic DRS measurements.

At block 309, the curve fitting module 221 may perform curve fitting on the logarithmic DRS measurements in the logarithmic domain. The curve fitting on the logarithmic DRS measurement in the logarithmic domain may be performed using a least squares technique and pre-defined parameters. Here, the pre-defined parameters are obtained from MC simulated DRS measurements using hundreds of millions of photons during training from the database 109.

At block 311, the non-logarithmic convertor module 223 may transform the curve-fitted logarithmic DRS measurements obtained from the block 309 to non-logarithmic domain to obtain optimized MC simulated DRS measurements.

At block 313, the univariate least squares module 225 may apply univariate least squares technique to the optimized MC simulated DRS measurements to obtain tuned MC simulated DRS measurements.

At block 315, the extractor module 227 may extract optical parameters by comparing the tuned MC simulated DRS measurements and the experimental DRS measurements.

Some of the advantages of the present disclosure are listed below.

In the present disclosure, the MC generated DRS with tens of thousands of photons has a very low runtime which might be at least 750 times faster and has very low computational complexity as compared to the traditional approach of using hundreds of millions of photons for the MC generated DRS.

In the present disclosure, the present optimizing method generates DRS with quality similar to the MC generated DRS using hundreds of millions of photons.

In the present disclosure, the present optimizing method requires very few data from the MC generated DRS using hundreds of millions of photons carried out during offline training.

Computing System

Figure 4:
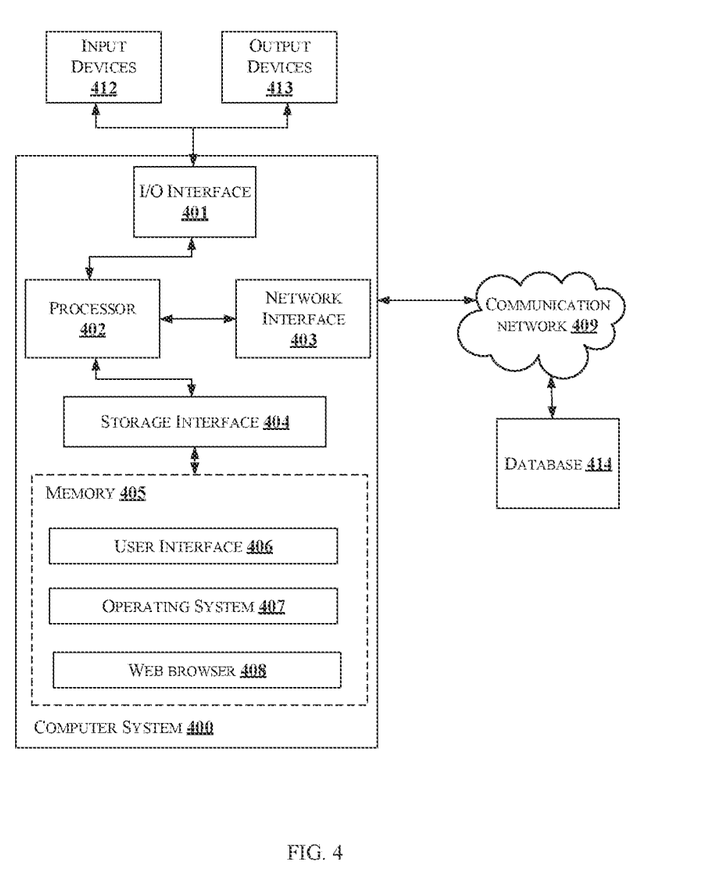
FIG. 4 illustrates a block diagram of an exemplary computer system according to an example embodiment.

FIG. 4 illustrates a block diagram of an exemplary computer system 400 according to an example embodiment. In an embodiment, the computer system 400 may be used to implement the DRS assistance system 107. The computer system 400 may include a central processing unit ("CPU" or "processor") 402. The processor 402 may include at least one data processor for optimizing Monte Carlo simulations for diffuse reflectance spectroscopy measurements. The processor 402 may include specialized processing units such as, integrated system (bus) controllers, memory management control units, floating point units, graphics processing units, digital signal processing units, etc.

The processor 402 may be disposed in communication with one or more input/output (I/O) devices via I/O interface 401. The I/O interface 401 employs communication protocols/methods such as, without limitation, audio, analog, digital, monoaural, Radio Corporation of America (RCA) connector, stereo, IEEE-1394 high speed serial bus, serial bus, Universal Serial Bus (USB), infrared, Personal System/2 (PS/2) port, Bayonet Neill-Concelman (BNC) connector, coaxial, component, composite, Digital Visual Interface (DVI), High-Definition Multimedia Interface (HDMI), Radio Frequency (RF) antennas, S-Video, Video Graphics Array (VGA), IEEE 802.11b/g/n/x, Bluetooth, cellular (e.g., Code-Division Multiple Access (CDMA), High-Speed Packet Access (HSPA+), Global System for Mobile communications (GSM), Long-Term Evolution (LTE), Worldwide interoperability for Microwave access (WiMax), or the like.

Using the I/O interface 401, the computer system 400 may communicate with one or more I/O devices such as input devices 412 and output devices 413. For example, the input devices 412 may be an antenna, keyboard, mouse, joystick, (infrared) remote control, camera, card reader, fax machine, dongle, biometric reader, microphone, touch screen, touchpad, trackball, stylus, scanner, storage device, transceiver, video device/source, etc. The output devices 413 may be a printer, fax machine, video display (e.g., Cathode Ray Tube (CRT), Liquid Crystal Display (LCD), Light-Emitting Diode (LED), plasma, Plasma Display Panel (PDP), Organic Light-Emitting Diode display (OLED) or the like), audio speaker, etc.

In some embodiments, the computer system 400 includes the DRS assistance system 107. The processor 402 may be disposed in communication with the communication network 409 via a network interface 403. The network interface 403 may communicate with the communication network 409. The network interface 403 may employ connection protocols including, without limitation, direct connect, Ethernet (e.g., twisted pair 10/100/1000 Base T), Transmission Control Protocol/Internet Protocol (TCP/IP), token ring, IEEE 802.11a/b/g/n/x, etc. The communication network 409 may include, without limitation, a direct interconnection, a Local Area Network (LAN), a Wide Area Network (WAN), a wireless network (e.g., using Wireless Application Protocol), the Internet, etc. Using the network interface 403 and the communication network 409, the computer system 400 may communicate with a database 414. The network interface 403 may employ connection protocols include, but not limited to, direct connect, Ethernet (e.g., twisted pair 10/100/1000 Base T), Transmission Control Protocol/Internet Protocol (TCP/IP), token ring, IEEE 802.11a/b/g/n/x, etc.

The communication network 409 includes, but is not limited to, a direct interconnection, an e-commerce network, a Peer to Peer (P2P) network, a Local Area Network (LAN), a Wide Area Network (WAN), a wireless network (e.g., using Wireless Application Protocol), the Internet, a Wi-Fi network, and the like. The first network and the second network may either be a dedicated network or a shared network, which represents an association of the different types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the first network and the second network may include a variety of network devices, including routers, bridges, servers, computing devices, storage devices, etc.

In some embodiments, the processor 402 may be disposed in communication with a memory 405 (e.g., RAM, ROM, etc.) via a storage interface 404. The storage interface 404 may connect to the memory 405 including, without limitation, memory drives, removable disc drives, etc., employing connection protocols such as, Serial Advanced Technology Attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 405 may store a collection of program or database components, including, without limitation, user interface 406, an operating system 407, etc. In some embodiments, computer system 400 may store user/application data, such as, the data, variables, records, etc., as described in this disclosure. Such databases may be implemented as fault-tolerant, relational, scalable, secure databases such as Oracle or Sybase.

The operating system 407 may facilitate resource management and operation of the computer system 400. Examples of operating systems include, without limitation, APPLE® MACINTOSH® OS X®, UNIX®, UNIX-like system distributions (e.g., BERKELEY SOFTWARE DISTRIBUTION® (BSD), FREEBSD®, NETBSD®, OPENBSD, etc.), LINUX® DISTRIBUTIONS (e.g., RED HAT®, UBUNTU®, KUBUNTU®, etc.), IBM® OS/2®, MICROSOFT® WINDOWS® (XP®, VISTA®/7/8, 10 etc.), APPLE® IOS®, GOOGLE™ ANDROID™, BLACKBERRY® OS, or the like.

In some embodiments, the computer system 400 may implement web browser 408 stored program components. Web browser 408 may be a hypertext viewing application, such as MICROSOFT® INTERNET EXPLORER®, GOOGLE™ CHROME™, MOZILLA® FIREFOX®, APPLE® SAFARI etc. Secure web browsing may be provided using Secure Hypertext Transport Protocol (HTTPS), Secure Sockets Layer (SSL), Transport Layer Security (TLS), etc. Web browsers 408 may utilize facilities such as AJAX, DHTML, ADOBE® FLASH®, JAVASCRIPT®, JAVA®, Application Programming Interfaces (APIs), etc. Computer system 400 may implement a mail server stored program component. The mail server may be an Internet mail server such as Microsoft Exchange, or the like. The mail server may utilize facilities such as ASP, ACTIVEX®, ANSI® C++/C#, MICROSOFT®, .NET, CGI SCRIPTS, JAVA®, JAVASCRIPT®, PERL®, PHP, PYTHON®, WEBOBJECTS®, etc. The mail server may utilize communication protocols such as Internet Message Access Protocol (IMAP), Messaging Application Programming Interface (MAPI), MICROSOFT® exchange, Post Office Protocol (POP), Simple Mail Transfer Protocol (SMTP), or the like. Computer system 400 may implement a mail client (not shown in FIG. 4) stored program component. The mail client may be a mail viewing application, such as APPLE® MAIL, MICROSOFT® ENTOURAGE®, MICROSOFT® OUTLOOK®, MOZILLA® THUNDERBIRD®, etc.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "non-transitory computer-readable medium" should be understood to include tangible items and exclude carrier waves and transient signals. Examples include Random Access Memory (RAM), Read-Only Memory (ROM), volatile memory, non-volatile memory, hard drives, CD ROMs, DVDs, flash drives, disks, and any other physical storage media.

The described operations may be implemented as a method, system, or article of manufacture using standard programming and/or engineering techniques to produce software, firmware, hardware, or any combination thereof. The described operations may be implemented as code maintained in a "non-transitory computer-readable medium," where a processor may read and execute the code from the computer-readable medium. The processor is at least one of a microprocessor and a processor capable of processing and executing the queries. A non-transitory computer-readable medium may include media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. Further, non-transitory computer-readable media include all computer-readable media except for transitory media. The code implementing the described operations may further be implemented in hardware logic (e.g., an integrated circuit chip, Programmable Gate Array (PGA), Application Specific Integrated Circuit (ASIC), etc.).

The terms "an embodiment," "embodiment," "embodiments," "the embodiment," "the embodiments," "one or more embodiments,", "some embodiments," and "one embodiment" mean "one or more (but not all) embodiments of the disclosure" unless expressly specified otherwise.

The terms "including," "comprising," "having," and variations thereof, mean "including but not limited to," unless expressly specified otherwise.

The enumerated listing of items does not imply that any or all of the items are mutually exclusive, unless expressly specified otherwise.

The terms "a," "an," and "the" mean "one or more," unless expressly specified otherwise.

A description of an embodiment with several components in communication with each other does not imply that all such components are required. On the contrary, a variety of optional components are described to illustrate the wide variety of possible embodiments of the disclosure.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the disclosure need not include the device itself.

The illustrated operations of FIG. 3 show certain events occurring in a certain order. In alternative embodiments, certain operations may be performed in a different order, modified, or removed. Moreover, steps may be added to the above described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the subject matter of the present disclosure. It is therefore intended that the scope of the present disclosure be limited not by this detailed description, but rather by any claims that issue on an application based here on. Accordingly, the description of the embodiments is intended to be illustrative, but not limiting, of the scope of the present disclosure, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERENCE NUMERALS

| Reference number | Description |
| --- | --- |
| 100 | Environment |
| 101 | DRS measurement system |
| 103 | DRS simulator system |
| 105 | Communication network |
| 107 | DRS assistance system |
| 109 | Database |
| 111 | I/O interface |
| 113 | Memory |
| 115 | Processor |
| 200 | Data |
| 201 | DRS simulated data |
| 203 | DRS measurement data |
| 205 | Optical data |
| 207 | Pre-defined data |
| 209 | Other data |
| 211 | Modules |
| 213 | Receiver module |
| 215 | Normalization module |
| 217 | Isotonic regression module |
| 219 | Logarithmic convertor module |
| 221 | Curve fitting module |
| 223 | Non-logarithmic convertor module |
| 225 | Univariate least squares module |
| 227 | Extractor module |
| 229 | Other modules |
| 400 | Computer system |
| 401 | I/O interface |
| 402 | Processor |
| 403 | Network interface |
| 404 | Storage interface |
| 405 | Memory |
| 406 | User interface |
| 407 | Operating system |
| 408 | Web browser |
| 409 | Communication network |
| 412 | Input devices |
| 413 | Output devices |
| 414 | Database |

We claim:

1. A method of transforming Monte Carlo (MC) simulations for diffuse reflectance spectroscopy (DRS), the method comprising:
   obtaining, by a DRS device, MC simulated DRS measurements using a pre-defined number of photons;
   pre-processing, by the DRS device, the MC simulated DRS measurements to obtain normalized DRS measurements;
   correcting, by the DRS device, non-monotonicity of the normalized DRS measurements to obtain monotonic DRS measurements;
   converting, by the DRS device, the monotonic DRS measurements to a logarithmic domain to obtain logarithmic DRS measurements;
   performing, by the DRS device, curve fitting on the logarithmic DRS measurements in the logarithmic domain to obtain curve-fitted logarithmic DRS measurements; and
   transforming, by the DRS device, the curve-fitted logarithmic DRS measurements to a non-logarithmic domain to obtain transformed MC simulated DRS measurements,
   wherein the correcting of non-monotonicity of the normalized DRS measurements is performed using an isotonic regression technique.

2. The method as claimed in claim 1, wherein the pre-defined number of photons is less than an optimum number of photons used for experimental DRS measurements.

3. The method as claimed in claim 2, wherein the pre-defined number of photons is ten thousand, and the optimum number of photons used for the experimental DRS measurements is one hundred million.

4. The method as claimed in claim 1, further comprising:
applying, by the DRS device, a univariate least squares technique to the transformed MC simulated DRS measurements to obtain tuned MC simulated DRS measurements; and
extracting, by the DRS device, optical parameters by comparing the tuned MC simulated DRS measurements and experimental DRS measurements.

5. The method as claimed in claim 1, wherein the curve fitting on the logarithmic DRS measurements in the logarithmic domain is performed using a least squares technique and pre-defined parameters.

6. The method as claimed in claim 5, wherein the pre-defined parameters are obtained from MC simulated DRS measurements using at least one hundred million photons during training.

7. A diffuse reflectance spectroscopy (DRS) device for transforming Monte Carlo (MC) simulations for DRS, the device comprising:
a memory configured to store instructions; and
a processor configured to execute the instructions to:
obtain MC simulated DRS measurements using a pre-defined number of photons;
pre-process the MC simulated DRS measurements to obtain normalized DRS measurements;
correct non-monotonicity of the normalized DRS measurements to obtain monotonic DRS measurements;
convert the monotonic DRS measurements to a logarithmic domain to obtain logarithmic DRS measurements;
perform curve fitting on the logarithmic DRS measurements in the logarithmic domain to obtain curve-fitted logarithmic DRS measurements; and
transform the curve-fitted logarithmic DRS measurements to a non-logarithmic domain to obtain transformed MC simulated DRS measurements,
wherein the correcting of non-monotonicity of the normalized DRS measurements is performed using an isotonic regression technique.

8. The DRS device as claimed in claim 7, wherein the pre-defined number of photons is less than an optimum number of photons used for experimental DRS measurements.

9. The DRS device as claimed in claim 8, wherein the pre-defined number of photons is ten thousand, and the optimum number of photons used for the experimental DRS measurements is one hundred million.

10. The DRS device as claimed in claim 7, wherein the processor is further configured to:
apply a univariate least squares technique to the transformed MC simulated DRS measurements to obtain tuned MC simulated DRS measurements; and
extract optical parameters by comparing the tuned MC simulated DRS measurements and experimental DRS measurements.

11. The DRS device as claimed in claim 7, wherein the curve fitting on the logarithmic DRS measurements in the logarithmic domain is performed using a least squares technique and pre-defined parameters.

12. The DRS device as claimed in claim 11, wherein the pre-defined parameters are obtained from MC simulated DRS measurements using at least one hundred million photons during training.

13. A method of transforming Monte Carlo (MC) simulations for diffuse reflectance spectroscopy (DRS), the method comprising:
obtaining MC simulated DRS measurements using a pre-defined number of photons;
pre-processing the MC simulated DRS measurements to obtain normalized DRS measurements;
correcting non-monotonicity of the normalized DRS measurements to obtain monotonic DRS measurements;
converting the monotonic DRS measurements to a logarithmic domain to obtain logarithmic DRS measurements;
performing curve fitting on the logarithmic DRS measurements in the logarithmic domain to obtain curve-fitted logarithmic DRS measurements;
transforming the curve-fitted logarithmic DRS measurements to a non-logarithmic domain to obtain transformed MC simulated DRS measurements; and
extracting optical parameters based on the transformed MC simulated DRS measurements,
wherein the correcting of non-monotonicity of the normalized DRS measurements is performed using an isotonic regression technique.

14. The method as claimed in claim 13, further comprising:
performing, on a sample, DRS measurements to obtain the MC simulated DRS measurements,
wherein the optical parameters are associated with glucose.

* * * * *